United States Patent [19]

Steinhardt

[11] 3,998,796
[45] Dec. 21, 1976

[54] NITROGEN AND SULFUR-CONTAINING AMPHOTERIC COMPOUNDS AND POLYMERS THEREOF

[75] Inventor: Charles Kendall Steinhardt, Houston, Tex.

[73] Assignee: The Lubrizol Corporation, Cleveland, Ohio

[22] Filed: July 7, 1975

[21] Appl. No.: 593,602

Related U.S. Application Data

[63] Continuation-in-part of Ser. No. 291,424, Sept. 22, 1972, abandoned.

[52] U.S. Cl. .......................... 260/79.7; 260/79.3 R; 260/79.3 M; 260/79.5 R; 260/79.5 C; 260/513 N

[51] Int. Cl.² .............. C07C 143/16; C08G 75/00; C08G 75/20

[58] Field of Search ..... 260/513 N, 79.7, 79.3 MU, 260/80 P, 80.3 N, 79.5 R, 79.5 C, 79.3 M, 79.3 R

[56] References Cited

UNITED STATES PATENTS

| 3,235,549 | 2/1966 | Broussalian | 260/513 N |
|---|---|---|---|
| 3,346,628 | 10/1967 | Riezebos et al. | 260/513 N |

FOREIGN PATENTS OR APPLICATIONS

| 1,090,779 | 11/1967 | United Kingdom | 260/513 N |

*Primary Examiner*—Ronald W. Griffin
*Attorney, Agent, or Firm*—James W. Adams, Jr.; William H. Pittman

[57] ABSTRACT

Novel nitrogen- and sulfur-containing amphoteric compounds are prepared by reacting ammonia with a heterocyclic intermediate prepared from a nitrile, an olefin and sulfur trioxide. These compounds are useful as surfactants; those that are polymerizable form polymers which are useful as co-flocculants in combination with inorganic flocculants.

13 Claims, No Drawings

NITROGEN AND SULFUR-CONTAINING AMPHOTERIC COMPOUNDS AND POLYMERS THEREOF

This application is a continuation-in-part of copending application Ser. No. 291,424, filed September 22, 1972, now abandoned.

This invention relates to new compositions of matter, both monomeric and polymeric, and to methods for their preparation. More particularly, it relates to compounds of the formula

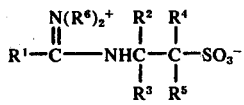  (I)

wherein each of $R^1$, $R^2$, $R^3$, $R^4$ and $R^5$ is hydrogen or a hydrocarbon-based radical and each $R^6$ is individually hydrogen or a hydrocarbon-based radical, or $N(R^6)_2$ is a heterocyclic radical.

As used herein, the term "hydrocarbon-based radical" denotes a radical having a carbon atom directly attached to the remainder of the molecule and having predominantly hydrocarbon character within the context of this invention. Such radicals include the following:

1. Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples include methyl, ethyl, propyl, butyl, hexyl, octyl, decyl, vinyl, allyl, pheny, benzyl, cyclohexyl, cyclopentyl, methylcyclopentyl, cyclopentadienyl, vinylphenyl, isopropenylphenyl, cinnamyl, naphthyl, tolyl, xylyl, $-C_6H_3(C_2H_5)_2$, $C_6H_4(CH_2)_{11}CH_3$,

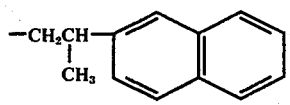

and

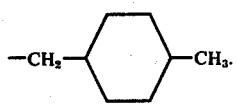

When more than one isomer is possible, all are included.

Many obvious variations of these radicals will be apparent to those skilled in the art and are included within the scope of the invention.

2. Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are halide, nitro, RO-,

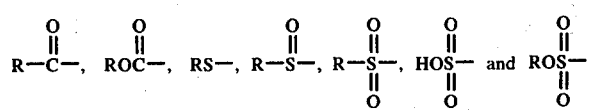

(R being a hydrocarbon and preferably a lower alkyl radical).

3. Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, oxygen, nitrogen and sulfur.

In general, no more than about three substituents or hetero atoms, and preferably no more than one, will be present for each 10 carbon atoms in the hydrocarbon-based radical.

In the preferred compounds of this invention, $R^1$ is a hydrocarbon radical, preferably an alkyl or alkenyl radical, having no more than about 30 carbon atoms and desirably no more than about 12 carbon atoms. Usually, it is a lower alkyl or alkenyl radical, the word "lower" denoting radicals containing up to 7 carbon atoms. The vinyl radical is particularly preferred.

When they are hydrocarbon-based radicals, $R^2$, $R^3$, $R^4$ and $R^5$ also usually have no more than about 30 and desirably no more than about 12 carbon atoms. They are preferably free from ethylenic and acetylenic unsaturation and are ordinarily hydrocarbon radicals, especially lower hydrocarbon radicals and preferably lower alkyl radicals. Most often, each of $R^2$ and $R^3$ is a hydrocarbon-based radical with the preferences noted hereinabove, especially methyl; and $R^4$ and $R^5$ are hydrogen.

$R^6$ is usually hydrogen but may be the other radicals mentioned, especially lower alkyl. Alternatively $N(R^6)_2$ may be a heterocyclic radical, most often a five- or six-membered heterocyclic ring (usually saturated) in which all remaining atoms are carbon or at most one is oxygen, sulfur or nitrogen. Examples of such radicals are pyrrolidyl, pyrrolyl, piperidyl, 2-methylpiperidyl, morpholinyl, thiamorpholinyl, tetrahydropyrimidinyl and tetrahydropyrazinyl.

Although the compounds of this invention are conveniently represented by formula I above, it will be readily understood to the chemist that they actually are resonance hybrids and tautomers which may be represented by a number of formulas. The following are illustrative (when $R^6$ is hydrogen):

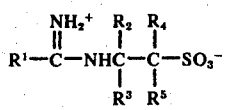

(I)

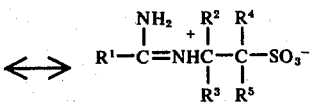

(II)

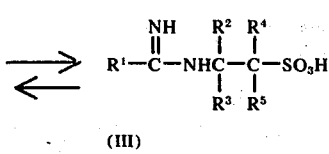
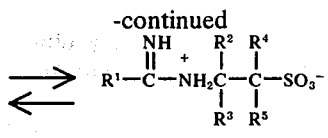

The nomenclature used herein is based on formula III; that is, the compounds of this invention are named as amidoalkylsulfonic acids for convenience although their chemical nature is, in fact, probably more accurately represented by formulas I, II and IV.

The compounds of this invention are illustrated by those in which the various R radicals are as identified in the following table.

| $R^1$ | $R^2$ | $R^3$ | $R^4$ | $R^5$ | $R^6$ or $N(R^6)_2$ |
|---|---|---|---|---|---|
| H | $CH_3$ | $CH_3$ | H | H | H |
| $CH_3$ | $CH_3$ | $C_2H_5$ | H | H | H |
| $CH_2=CH$ | H | H | H | H | H |
| $CH_2=C-$<br>    $\|$<br>    $CH_3$ | $CH_3$ | H | $CH_3$ | H | $CH_3$ |
| $CH_2=CH$ | $C_6H_5$ | $CH_3$ | H | H | $CH_3$ |
| $C_6H_5$ | $ClC_6H_4$ | $CH_3$ | $CH_3$ | H | 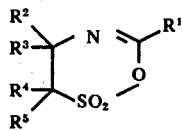 |
| $CH_2=CH$ | cyclohexyl | H | $C_2H_5$ | $CH_3$ | H |
| $CH_2=CH$ | $-(CH_2)_5-$ | | H | H | H |
| $CH_2=CH$ | $CH_3OC_6H_4$ | H | H | $CH_3$ | $CH_3$ |

The compounds of this invention may be prepared by reacting ammonia or a primary or secondary amine with a heterocyclic compound of the formula

wherein $R^{1-5}$ are as previously defined. The preparation of these heterocyclic compounds is described in U.S. Pat. No. 3,235,549 and in British Pat. No. 1,090,779. In general, about one mole of the heterocyclic compound is reacted with one mole of ammonia or amine, although an excess of one or the other reagent may be used if desired. The reaction is generally carried out at a temperature between about −70° and +50° C., in a substantially inert liquid diluent such as an aliphatic or aromatic hydrocarbon or halogenated hydrocarbon. The compound of this invention usually separates as it is formed and can easily be isolated by filtration and purified, if desired, by conventional methods.

The compounds of this invention may also be prepared by reacting sulfur trioxide (either pure or in the form of a complex with pyridine, dioxane, thioxane, alkyl phosphates or the like) with a nitrile of the formula $R^1CN$ and an olefin of the formula

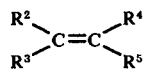

to form an intermediate which is then reacted with ammonia or a primary or secondary amine. The intermediate is probably the heterocycle of formula V above. It is conveniently formed at a temperature between about −85° C. and room temperature, usually between −85° and −30° C. when pure $SO_3$ is used and somewhat higher (e.g., about 0°–20° C.) when a complex thereof is used, by the reaction of the nitrile, olefin and sulfur trioxide, ordinarily using approximately equimolar proportions of the olefin and sulfur trioxide and a somewhat larger amount of the nitrile, frequently as much as a tenfold excess or even more. The intermediate is conveniently prepared in a solvent, usually the same solvent used in the subsequent reaction with ammonia or the amine. The intermediate need not be isolated but may be directly reacted with ammonia or the amine to afford the product of this invention.

The preparation of the compounds of this invention is illustrated by the following examples.

EXAMPLE 1

A solution of 88.4 grams (1.1 moles) of sulfur trioxide in 1100 ml. of methylene chloride is prepared at −45° C. and is added over ½ hour, at −75° to −69° C., to 1100 ml. of acrylonitrile. Isobutene, 77 grams (1.34 moles), is then bubbled into the resulting clear yellow solution over 50 minutes at −75° to −69° C. Stirring is continued for 1-½ hours at −75° C. and the mixture is then warmed to +20° C. and filtered. It is purged with nitrogen and cooled to −30° C., and then 20 grams (1.2 moles) of ammonia is added above the surface of the liquid. The mixture warms to +40° C. during the addition. The solid which precipitates is filtered, washed with acetone and dried in a vacuum oven. There is obtained 214 grams (97% of theoretical) of the desired 2-acrylimidoamino-2-methylpropanesulfonic acid.

EXAMPLE 2

The procedure of Example 1 is repeated, except that acetonitrile is substituted for the acrylonitrile on an equimolar basis. The product is 2-acetimidoamino-2-methylpropanesulfonic acid.

EXAMPLE 3

The procedure of Example 1 is repeated, except that 5.0 moles of benzonitrile is substituted for the acrylonitrile and the reaction takes place at a temperature between −30° and −40° C. The product is the desired 2-benzimidoamino-2-methylpropanesulfonic acid.

EXAMPLE 4

A solution of 115 grams (1.44 moles) of sulfur trioxide in 600 ml. of trichlorofluoromethane is added to 1440 ml. of acrylonitrile over 5 minutes, at −70° to −60° C. Propylene, 73 grams (1.73 moles), is then added over 25 minutes at −75° to −65° C. The mixture is allowed to warm to 20° C. and 25 grams (1.45 moles) of ammonia is added. The solid which precipitates is removed by filtration, washed with acrylonitrile and dried in a vacuum oven; it is the desired 2- acrylimidoaminopropanesulfonic acid. The yield is 227 grams, or 82% of theoretical.

EXAMPLE 5

Following the procedure of Example 4; 2-acrylimidoaminobutanesulfonic acid is prepared from 117.3 grams (1.46 moles) of sulfur trioxide, 600 ml. of trichlorofluoromethane, 1460 ml. of acrylonitrile, 87 grams (1.54 moles) of 1-butene, and 26 grams (1.5 moles) of ammonia. The yield is 241 grams, or 80% of theoretical.

EXAMPLE 6

The procedure of Example 4 is repeated except that styrene is substituted on an equimolar basis for propylene. The product is the desired 2-acrylimidoamino-2-phenylethanesulfonic acid.

The compounds of this invention are generally water-soluble and are amphoteric. They may be used as surfactants.

Compounds of this invention wherein $R^1$ is vinyl or a similar polymerizable radical may be polymerized under free-radical conditions, either alone or in the presence of other monomers. The term "polymer", as used herein, includes addition homopolymers, copolymers, terpolymers and other interpolymers.

Polymerization by the free-radical method may be effected in bulk, solution, suspension or emulsion, by contacting the monomer or monomers with a polymerization initiator either in the absence or presence of a diluent at a temperature of about 0°–200° C. Suitable initiators include benzoyl peroxide, tertiary butyl hydroperoxide, acetyl peroxide, hydrogen peroxide, azobisisobutyronitrile, persulfate-bisulfite, persulfate-sodium formaldehyde sulfoxylate, chlorate-sulfite and the like.

A large variety of polymerizable compounds can be used to form interpolymers of this invention. They include (1) esters of unsaturated alcohols, (2) esters of unsaturated acids, (3) esters of unsaturated polyhydric alcohols, (4) vinyl cyclic compounds, (5) unsaturated ethers, (6) unsaturated ketones, (7) unsaturated amides, (8) unsaturated aliphatic hydrocarbons, (9) vinyl halides, (10) unsaturated acids, (11) unsaturated acid anhydrides, (12) unsaturated acid chlorides, and (13) unsaturated nitriles. Specific illustrations of such compounds are:

1. Unsaturated alcohols and esters thereof: Allyl, methallyl, crotyl, 1-chloroallyl, 2-chloroallyl, cinnamyl, vinyl, methylvinyl, 1-phenallyl, butenyl alcohols, and esters of such alcohols with saturated acids such as acetic, propionic, butyric, valeric, caproic and stearic; with unsaturated acids such as acrylic, alpha-substituted acrylic (including alkylacrylic, e.g., methacrylic, ethylacrylic, propylacrylic, etc., and arylacrylic such as phenylacrylic), crotonic, oleic, linoleic and linolenic; with polybasic acids such as oxalic, malonic, succinic, glutaric, adipic, pimelic, suberic, azelaic and sebacic; with unsaturated polybasic acids such as maleic, fumaric, citraconic, mesaconic, itaconic, methylenemalonic, acetylenedicarboxylic and aconitic; and with aromatic acids, e.g., benzoic, phenylacetic, phthalic, terephthalic and benzoylphthalic acids.

2. Esters of saturated alcohols, such as methyl, ethyl, propyl, isopropyl, butyl, isobutyl, sec-butyl, tert-butyl, 2-ethylhexyl, cyclohexyl or behenyl alcohols, with unsaturated aliphatic monobasic and polybasic acids, examples of which are illustrated above.

3. Esters of unsaturated polyhydric alcohols, e.g., butenediol, with saturated and unsaturated aliphatic and aromatic, monobasic and polybasic acids, illustrative examples of which appear above.

4. Vinyl cyclic compounds including styrene, o-, m-, p-chlorostyrenes, bromostyrenes, fluorostyrenes, methylstyrenes, ethylstyrenes and cyanostyrenes; di-, tri-, and tetra-chlorostyrenes, bromostyrenes, fluorostyrenes, methylstyrenes, ethylstyrenes, cyanostyrenes; vinylnaphthalene, vinylcyclohexane, divinylbenzene, trivinylbenzene, allylbenzene, and heterocycles such as vinylfuran, vinylpyridine, vinylbenzofuran, N-vinylcarbazole, N-vinylpyrrolidone and N-vinyloxazolidone.

5. Unsaturated ethers such as methyl vinyl ether, ethyl vinyl ether, cyclohexyl vinyl ether, octyl vinyl ether, diallyl ether, ethyl methallyl ether and allyl ethyl ether.

6. Unsaturated ketones, e.g., methyl vinyl ketone and ethyl vinyl ketone.

7. Unsaturated amides, such as acrylamide, methacrylamide, N-methylacrylamide, N-phenylacrylamide, N-allylacrylamide, N-methylolacrylamide, N-allylcaprolactam, diacetone acrylamide, hydroxymethylated diacetone acrylamide and 2-acrylamido-2-methylpropanesulfonic acid.

8. Unsaturated aliphatic hydrocarbons, for instance, ethylene, propylene, butenes, butadiene, isoprene, 2-chlorobutadiene and alpha-olefins in general.

9. Vinyl halides, e.g., vinyl fluoride, vinyl chloride, vinyl bromide, vinylidene chloride, vinylidene bromide, allyl chloride and allyl bromide.

10. Unsaturated acids (for example, acrylic, methacrylic, propylacrylic), examples of which appear above.

11. Unsaturated acid anhydrides, e.g., maleic, citraconic, itaconic, cis-4-cyclohexene-1,2-dicarboxylic and bicyclo(2,2,1)-5-heptene-2,3-dicarboxylic anhydrides.

12. Unsaturated acid halides such as cinnamoyl, acrylyl, methacrylyl, crotonyl, oleyl and fumaryl chlorides or bromides.

13. Unsaturated nitriles, e.g., acrylonitrile, methacrylonitrile and other substituted acrylonitriles.

The especially preferred polymers are the homopolymers and copolymers with acrylic monomers; that is, with acids such as acrylic and methacrylic acids and their esters, amides and nitriles. Of these, the most desirable as flocculants are homopolymers and copolymers with acrylamide and with substituted acrylamides, especially acrylamidoalkanesulfonic acids.

The preparation of the polymers of this invention is illustrated by the following examples. Unless otherwise indicated, inherent viscosities are determined on a solution of 0.25 gram of the polymer in 100 ml. of 10% aqueous sodium chloride solution at 30° C.

EXAMPLE 7

A solution of 20 parts (by weight) of 2-acrylimidoamino-2-methylpropanesulfonic acid and 0.25 part each of potassium persulfate and sodium metabisulfite (added as 0.02 M aqueous solutions) in 150 parts of water is heated at 50° C. under nitrogen, with stirring, for 3 hours. The desired homopolymer precipitates and is removed by filtration, washed with water and acetone, and dried in a vacuum oven. It has an inherent viscosity of 3.40.

EXAMPLES 8–11

Copolymers of 2-acrylimidoamino-2-methylpropanesulfonic acid with acrylamide are prepared in aqueous solution, using a potassium persulfate-sodium metabisulfite catalyst and a procedure similar to that of Example 7. The details are given in the following table. Monomer percentages are by weight.

| Example | % Product of Ex. 1 | % acrylamide | Inherent viscosity |
|---------|--------------------|--------------|--------------------|
| 8       | 50                 | 50           | 4.92               |
| 9       | 75                 | 25           | 5.86               |
| 10      | 90                 | 10           | 5.60               |
| 11      | 95                 | 5            | 4.26               |

EXAMPLE 12

Following a procedure similar to that of Example 7, a copolymer is prepared in an aqueous medium from 20 parts (by weight) of 2-acrylimidoamino-2-methylpropanesulfonic acid and 5 parts of sodium 2-acrylamido-2-methylpropanesulfonate, using a potassium persulfate-sodium metabisulfite catalyst. The aqueous solution thickens and the polymer precipitates when acetone is added thereto. It is recovered and crushed. The product has an inherent viscosity of 4.88.

EXAMPLE 13

2-Acrylimidoamino-2-methylpropanesulfonic acid, 5 grams, and 90 grams of a 50% aqueous solution of sodium 2-acrylamido-2-methylpropanesulfonate are placed in a flask and 500 ml. of benzene is added, followed by 5 ml. of a 0.01 M benzene solution of bis-(4-t-butylcyclohexyl) peroxydicarbonate and 0.5 gram of sodium lauryl sulfate. The mixture is stirred under nitrogen at 50° C. as the polymer precipitates and congeals; it is recovered and pulverized. The product has an inherent viscosity (3% sodium chloride solution) of 8.43.

The polymers of this invention, like the nonpolymerizable compounds of this invention, are useful as coflocculants for aqueous systems. When the polymers are not soluble in water, they can be solubilized by adding a small amount of an inorganic salt such as sodium chloride or sodium carbonate or by raising the pH by the addition of ammonia, amines, or alkali metal hydroxides. For example, kaolin is rapidly flocculated from an aqueous suspension thereof by the addition of 10 ppm. of alum and 0.2 ppm. of the polymer of Example 7 (added as an aqueous solution containing 20 ppm. of sodium carbonate and 100 ppm. of the polymer), or by the addition of 2 ppm. of ferric chloride and 0.2 ppm. of the copolymer of Example 9.

What is claimed is:

1. A compound of the formula

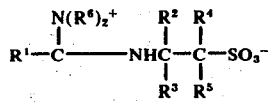

wherein each of $R^1$, $R^2$, $R^3$, $R^4$ and $R^5$ is hydrogen or a hydrocarbon-based radical and each $R^6$ is individually hydrogen or a hydrocarbon-based radical, or $N(R^6)_2$ is a five- or six-membered heterocyclic ring in which all atoms in the $(R^6)_2$ moieties are carbon or at most one such atom is oxygen, sulfur or nitrogen; said hydrocarbon-based radicals having a carbon atom directly attached to the remainder of the molecule and having predominantly hydrocarbon character.

2. A compound according to claim 1 wherein $R^1$ is a hydrocarbon radical; each of $R^2$ and $R^3$ is a hydrocarbon radical free from ethylenic and acetylenic unsaturation and having no more than about 30 carbon atoms; each of $R^4$ and $R^5$ is hydrogen or a hydrocarbon radical free from ethylenic and acetylenic unsaturation and having no more than about 30 carbon atoms; and each $R^6$ is individually hydrogen or a lower alkyl radical.

3. A compound according to claim 2 wherein $R^1$ is a lower alkyl or lower alkenyl radical; each of $R^2$ and $R^3$ is a lower hydrocarbon radical; and each of $R^4$ and $R^5$ is hydrogen or a lower alkyl radical.

4. A compound according to claim 3 wherein $R^1$ is a lower alkenyl radical; each of $R^2$ and $R^3$ is a lower alkyl radical; and $R^4$ and $R^5$ are hydrogen.

5. A compound according to claim 4 wherein each $R^6$ is hydrogen.

6. A compound according to claim 5 wherein $R^1$ is vinyl and each of $R^2$ and $R^3$ is methyl.

7. An addition polymer of a compound according to claim 6.

8. A polymer according to claim 7 which is an interpolymer with at least one polymerizable unsaturated monomer.

9. A polymer according to claim 8 wherein the polymerizable unsaturated monomer is an acrylic compound.

10. A polymer according to claim 9 wherein the acrylic compound is an acrylamide.

11. An addition polymer of a compound according to claim 4.

12. A polymer according to claim 11 which is an interpolymer with at least one polymerizable unsaturated monomer.

13. A polymer according to claim 12 wherein the polymerizable unsaturated monomer is an acrylic compound.

* * * * *